US006402705B1

(12) United States Patent
Caillouette

(10) Patent No.: US 6,402,705 B1
(45) Date of Patent: Jun. 11, 2002

(54) BODY MOISTURE TEST APPARATUS AND METHOD

(76) Inventor: James C. Caillouette, 685 Oak Knoll Cir., Pasadena, CA (US) 91106

( * ) Notice: Subject to any disclaimer, the term of this patent is extended or adjusted under 35 U.S.C. 154(b) by 0 days.

(21) Appl. No.: 09/436,332

(22) Filed: Nov. 8, 1999

Related U.S. Application Data

(63) Continuation-in-part of application No. 09/072,257, filed on May 4, 1998, now Pat. No. 6,013,036, which is a continuation-in-part of application No. 08/890,748, filed on Jul. 11, 1997, now Pat. No. 5,916,176, which is a continuation-in-part of application No. 08/699,251, filed on Aug. 19, 1996, now Pat. No. 5,735,801, which is a continuation-in-part of application No. 08/570,534, filed on Dec. 11, 1995, now Pat. No. 5,762,614, which is a continuation-in-part of application No. 08/537,379, filed on Oct. 27, 1995, now Pat. No. 5,577,512, which is a continuation-in-part of application No. 08/376,830, filed on Jan. 23, 1995, now Pat. No. 5,664,579, which is a continuation-in-part of application No. 08/295,399, filed on Aug. 25, 1994, now Pat. No. 5,425,377.

(51) Int. Cl.[7] .............................................. A61B 5/00
(52) U.S. Cl. ...................................................... 600/584
(58) Field of Search ................................. 600/572, 574, 600/584; 33/511, 512

(56) References Cited

U.S. PATENT DOCUMENTS

| | | |
|---|---|---|
| 2,664,876 A | 1/1954 | Hardy |
| 2,945,491 A | 7/1960 | Gibbs |
| 3,037,496 A | 6/1962 | Melges |
| 3,117,569 A | 1/1964 | Wegner |
| 3,319,621 A | 5/1967 | Schwerin |
| 3,507,269 A | 4/1970 | Berry |
| 3,509,872 A | 5/1970 | Truhan |
| 3,792,699 A | 2/1974 | Tobin et al. |
| 4,820,259 A | 4/1989 | Stevens |
| 4,862,899 A | 9/1989 | Bucaro |
| 5,063,930 A | 11/1991 | Nucci |
| 5,124,254 A | 6/1992 | Hewlins et al. |
| 5,147,288 A | 9/1992 | Schiavo |
| 5,253,652 A | 10/1993 | Fast |
| 5,334,502 A | * 8/1994 | Sangha ....................... 600/584 |
| 5,425,377 A | 6/1995 | Caillouette |
| 5,577,512 A | 11/1996 | Caillouette |
| 5,664,579 A | 9/1997 | Caillouette |
| 5,735,801 A | 4/1998 | Caillouette |
| 5,762,614 A | 6/1998 | Caillouette |
| 5,823,953 A | * 10/1998 | Roskin et al. ............... 600/584 |
| 5,916,176 A | 6/1999 | Caillouette |

OTHER PUBLICATIONS

"Vulvovaginitis", vol. 1, Chapter 37, Ronald M. Meltzer.
"Urinary Incontinence and Related Urogenital Synptoms in Elderly Women", Ulla Molander, Scandinavian Association of Obstetricians and Gynecolgists, Supplement 158, vol. 72, 1993.
"Estrogen Deprivation and Vaginal Function in Postmenopausal Women", James P. Semmens, MD, Gorm Wagner, MD.
Peter Smith, Dept. of Obstetrics & Gynecology, University Hospital, S–751 85 Uppsala, Sweden "Estrogens and the Urogenital Tract".
Gloria Bachman, Maturitas 22 Suppl. (1995) S21–S29 "the Estradiol Vaginol Ring—A Study of Existing Clinical Data".

* cited by examiner

Primary Examiner—Max Hindenburg
(74) Attorney, Agent, or Firm—William W. Haefliger

(57) ABSTRACT

In the method of measuring pH of vaginal or other tissue moisture, the steps that include providing an indicator that exhibits a characteristic color when contacted with the moisture, the color being a function of moisture pH; obtaining a vaginal or other tissue moisture sample and transferring moisture from the sample to an indicator, outside the body, whereby the indicator then exhibits a characteristic color, which is a function of pH of the moisture; and providing a color comparison measurement means, and comparing the indicator characteristic color with color comparison measurement means. Also provided are test kit structures to enable performance of such pH measurement, as used for estrogen need determination and the presence or absence of amniotic fluid; and also to determine presence of amines produced by pathogenic bacteria, or flagellates (trichomonas).

31 Claims, 3 Drawing Sheets

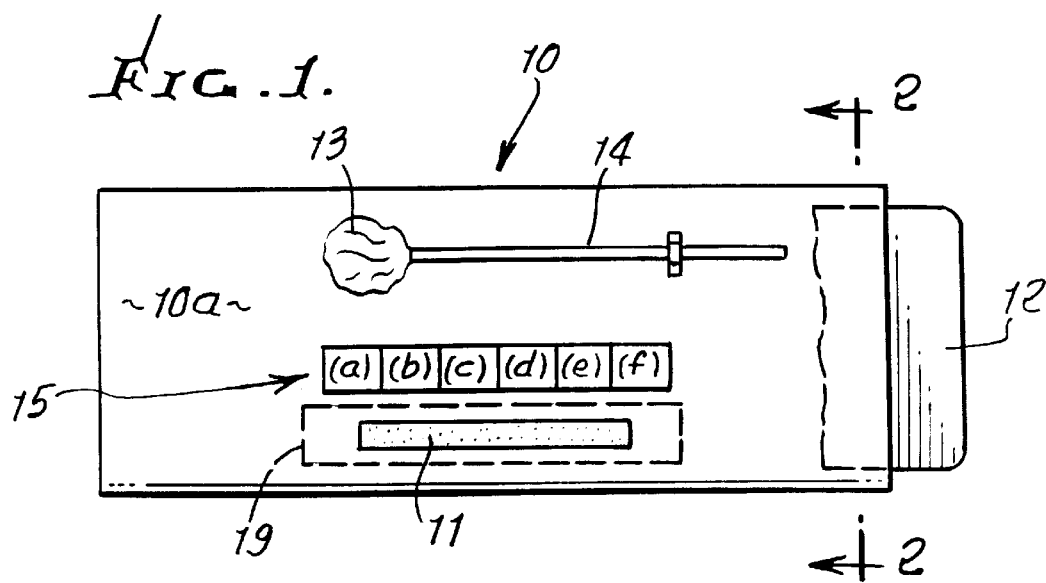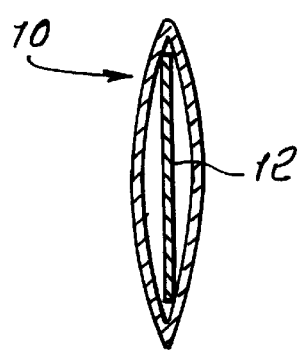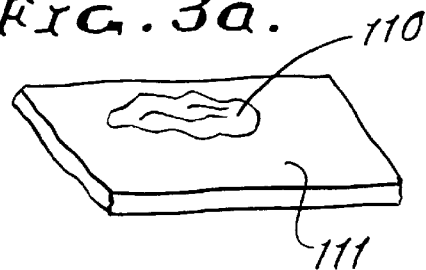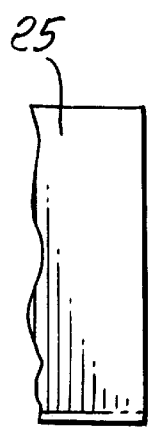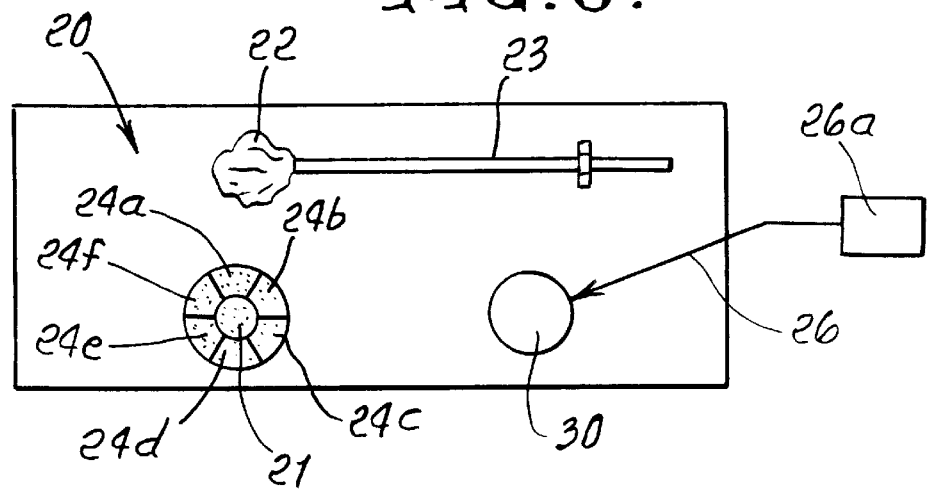

BODY MOISTURE TEST APPARATUS AND METHOD

This application is a continuation-in-part of prior U.S. application Ser. No. 09/072,257 filed May 4, 1998, now U.S. Pat. No. 6,013,036 which is a continuation-in-part of prior U.S. application Ser. No. 08/890,748 filed Jul. 11, 1997, now U.S. Pat. No. 5,916,176, which is a continuation-in-part of prior U.S. application Ser. No. 08/699,251 filed Aug. 19, 1996, now U.S. Pat. No. 5,735,801, which is a continuation-in-part of prior U.S. application Ser. No. 08/570,534 filed Dec. 11, 1995, now U.S. Pat. No. 5,762,614, which is a continuation-in-part of prior U.S. application Ser. No. 08/537,379 filed Oct. 27, 1995, now U.S. Pat. No. 5,577,512, which is a continuation-in-part of prior U.S. application Ser. No. 08/376,830 filed Jan. 23, 1995, now U.S. Pat. No. 5,664,579, which is a continuation-in-part of prior U.S. application Ser. No. 08/295,399 filed Aug. 25, 1994, now U.S. Pat. No. 5,425,377.

BACKGROUND OF THE INVENTION

This invention relates generally to pH measurement of body fluid, such as vaginal moisture, and more particularly to a rapid and easily performed method of obtaining such measurement, as well as apparatus to perform the method. The invention also relates to detection of pathogenic bacteria in the vagina, for example in association with such pH measurement, whereby more complete testing can easily be achieved.

There is continual need for improvements in testing and measurement methods, as referred to; and in particular there is need for effecting such testing and measurements without introduction of possibly toxic materials or substances into the vagina or other body cavities or parts.

SUMMARY OF THE INVENTION

It is a major object of the invention to provide improved testing and measurement methods and procedures that meet the above need, and overcome prior difficulties, as referred to.

Basically, an important method provided by the invention includes the steps a) providing an indicator that exhibits a characteristic color when contacted with vaginal or other body tissue moisture, the color being a function of moisture pH, b) obtaining a vaginal or tissue moisture sample and transferring moisture from the sample to the indicator, outside the vagina or tissue sampled, whereby the indicator then exhibits a characteristic color, which is a function of pH of the moisture, c) providing a color comparison measurement means, and comparing the indicator characteristic color with the color comparison measurement means.

As will appear, a vaginal or tissue moisture receiver is typically provided to be supported on a carrier, to be manipulated to obtain the vaginal or tissue moisture sample on the receiver, for transfer to the indicator, outside the vagina or other anatomic site.

It is another important object to provide a package which includes structure supporting said indicator and said carrier for the receiver, and including the step of removing the carrier from the package for use in obtaining said moisture sample on the receiver.

As will be seen, the color comparison measurement means is typically provided to extend proximate said indicator, in or on the package; and may be provided to include portions of varying color that are arranged in one of the following ways:

i) in a generally linear sequence, ii) in a sequence to at least partially surround the indicator.

Further, the indicator may include multiple sections, and the color comparison measurement means typically includes color swatches, at least one swatch located proximate each indicator.

Another object is to provide the carrier in the form of an inserter, or stick, and the receiver is supported proximate an end of the stick, the receiver provided in the form of a swab, and a shoulder is provided on the stick to limit depth of insertion of the swab, into the vagina.

A further object is to provide a second indicator supported by the package, the second indictor including a reactant or reactants characterized as changing color when contacted with moisture containing amine, and including transferring moisture from the sample to the second indicator, outside the vagina, whereby a change in color at the second indicator indicates the presence of pathogenic bacteria in such moisture.

It is an additional object to repeat the basic pH detector method, at intervals over a time period sufficient to detect changes in vaginal or other tissue moisture pH levels, indicative of need for estrogen, antibiotics or other therapy.

Yet another object is to provide apparatus that includes:

a) a package, b) a pH detector on the package, c) the detector including a pH indicator responsive to reception of vaginal or other tissue moisture, to change color indicative of pH level, when such moisture is transferred to the indicator, outside the body.

A yet further object is to provide a comprehensive method that includes, in combination a) providing an indicator that exhibits a characteristic color when contacted with vaginal or other tissue moisture, said color being a function of moisture pH, b) obtaining a vaginal or other tissue moisture sample and transferring moisture from the sample to the indicator, outside the body, whereby the indicator then exhibits said characteristic color, which is a function of pH of said moisture, c) providing a color comparison measurement means, and comparing said indicator characteristic color with said color comparison measurement means.

In the above form of apparatus, the pH detector may typically include an indicator or indictors responsive to reception of vaginal or tissue moisture to change to a color or colors indicative of pH level, and there being color comparison measurement means associated with said indicator or indicators, on a package.

Further, the color comparison measurement means typically may extend close to and at least part way about said indicator, whereby a small indicator area may be effectively employed for reception of a minimum amount of collected moisture.

An additional object is to provide a pH test for presence of amniotic fluid, as may collect on a surface.

These and other objects and advantages of the invention, as well as the details of an illustrative embodiment, will be more fully understood from the following specification and drawings, in which:

DRAWING DESCRIPTION

FIG. 1 is a plan view of a kit or package in which one form of the invention is embodied;

FIG. 2 is a section taken on lines 2—2 of FIG. 1;

FIG. 3 is a view like FIG. 1, showing a modified form of the kit;

FIG. 3a shows amniotic and/or other leaking fluid collection on a surface;

DETAILED DESCRIPTION

Figure 4:
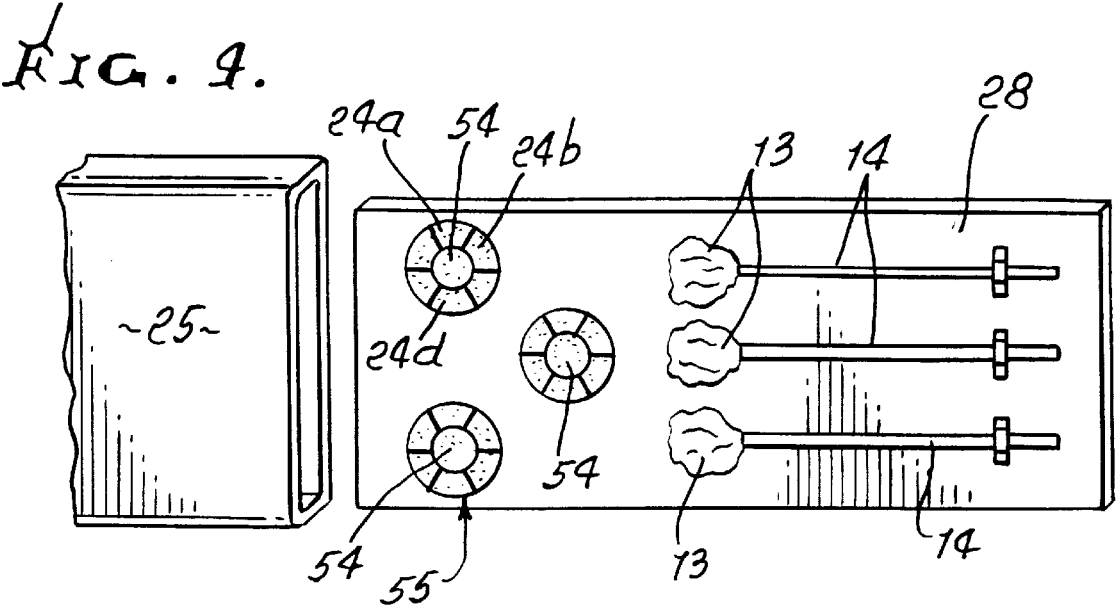
FIG. 4 is a view like FIG. 1 showing a still further modification.

In FIG. 1, a kit or package 10 is elongated, and carries a pH detector such as a strip 11 of indicator material. Strip 11 may be located on the exterior surface of the package 10, or within the package as on a removable card 12. Also removably carried by the package, as on the removable card, is a means or device for obtaining a sample of vaginal or tissue moisture, for transfer to the indicator strip. In other words, the indicator is typically not inserted into the vagina, or other cavity since only the inert material of the moisture receiver is inserted, whereby any potential or possible toxic effect is obviated, i.e. is not presented or encountered.

The moisture receiver is shown in the form of a moisture collecting swab 13, on an elongated inserter, such as a stick 14. In use, the card is removed endwise from a receptacle 10a which may be formed by the kit, and the inserter 14 with swab 13 attached is removed from the card. Since the indicator strip 11 is preferably located on the card, it too is removed from the protective receptacle 10a and presented for use, when the card is removed from the receptacle 10a.

After a sample of vaginal or other cavity moisture is obtained on the swab, it is transferred to the indicator strip, by rubbing of the swab on the indicator. The indicator is responsive to reception of such moisture to change to a color corresponding to moisture pH level. One such useful indicator is a NITRAZINE® strip adhered to the card. Alternatively, it may be adhered to the outer surface of the receptacle or package 10.

A pH correlating color comparison measurement means is provided as at 15 in sufficiently close association with said detector or indicator 11 to allow visual comparison of the changed color exhibited by the indicator with a pH correlated color provided by said measurement means. See for example the series of bands, each having a different color corresponding to a pH level color to which the detector strip may change. See for example the indicated pH levels 4.5, 5.0, 5.5, 6.0, 6.5, 7.0 and 7.5 adjacent the colored bands. The bands may be provided on a strip adhered to the sleeve or receptacle 10a. Paper strips providing such elements are known, and sold under the name HYDRION PAPERS®. "HYDRION PAPERS" is a trademark of Micro Essential Laboratory, Inc., Brooklyn, N.Y. 11210. The band for pH 4.5 is typically bright yellow; the band for pH 6.0 is olive in color; and the band for pH 7.5 is navy blue, and color gradations appear on the intermediate bands.

The indicator 11, after its exposure to moisture and color change, as referred to, may be brought into lateral registration with the color comparison bands, as by movement of the card 12 relative to the receptacle or sleeve 10a, and to the bands on that sleeve. For example, the card carrying the indicator may be moved within the sleeve, which guides its endwise movement, and brings the characteristically color changed portion of the indicator into registration with successive bands, for matching purposes. The card may also be moved outside the receptacle to effect the color matching. Alternatively, the indicator and bands may be affixed or positioned on the same object, such as the card, or the outer surface of the receptacle 10a.

A zone 19 of the receptacle 11a may be made transparent to allow visual observation of the indicator through that zone, and adjacent the bands, as the card is moved within the receptacle.

FIG. 3 shows a modification in which a card or receptacle 20 carries on its surface a fixed indicator 21 as referred to, in a localized area, to receive moisture transfer from a swab 22 on a stick 23 associated with or removable from 20. The color comparison bands seen at 24a–24f are here presented in a generally circular sequence, extending about, or at least part way about, and close to, the localized indicator 21. This facilitates ease of color comparison, and requires no movement of the indicator relative to the bands 24a–24f, since each of the bands extends close to the indicator. Card 20 may be received endwise within a protective receptacle seen at 25.

Also shown in FIG. 3 is a second indicator 30 carried by the receptacle 20 or card surface. That indicator constitutes an amine detector, to receive transfer of vaginal moisture. The second detector or indicator may typically include, or otherwise receive, a reactant or reactants characterized as changing color when contacted by vaginal moisture that contains an amine, such as putrecine or cadaverine. Such color change indicates the presence of pathogenic bacteria or flagelate protozoa (genus trichomonas) in the vagina or other site. The second indicator may be selected from the group consisting of Bromocresol Green, Bromocresol Purple, Nitrazine Yellow, Bromophenol Blue, and equivalents. Reactant or reactants may include an alkali substance selected from the group that consists essentially of potassium hydroxide, sodium aluminate, magnesium hydroxide, sodium hypochlorite and sodium carbonate, applied as at 26, and from a source 26a. See also Caillouette U.S. Pat. Nos. 5,782,801 and 5,827,200 with regard to application of reactants, such patents incorporated herein by reference.

Accordingly, the embodiment shown in FIG. 3 represents a dual test, one for pH, and the other being a colorometric test for presence of amine—the product of pathogenic organisms bacteria, or flagellates (trichomonas).

It will be understood that the pH determination method may be repeated at intervals (such as daily) over a time period (and using kits or packaging as described) sufficient to detect changes in vaginal moisture pH level or levels, indicative of need for estrogen therapy. See in this regard U.S. Pat. No. 5,916,176, to Caillouette, incorporated herein by reference.

FIG. 4 shows a number of indicators 54 on one card 28, and circularly arranged color test bands 55 about each indicator, as in FIG. 3. This provides for test verification, as by multiple testing on one card. Multiple swabs 13 are also usable, for such tests.

Figure 5:
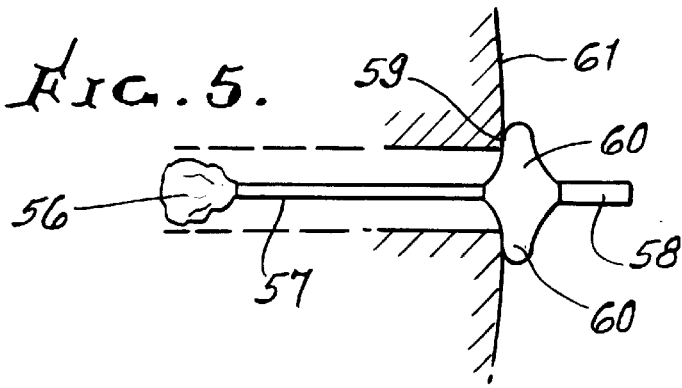
FIG. 5 is a view showing a modified inserter.

FIG. 5 shows a swab 56 on an elongated inserter 57, with a handle area 58. Shoulders 59 on sideward projections 60 act to limit insertion of the swab, by engagement with the body, at 61.

Figure 6:
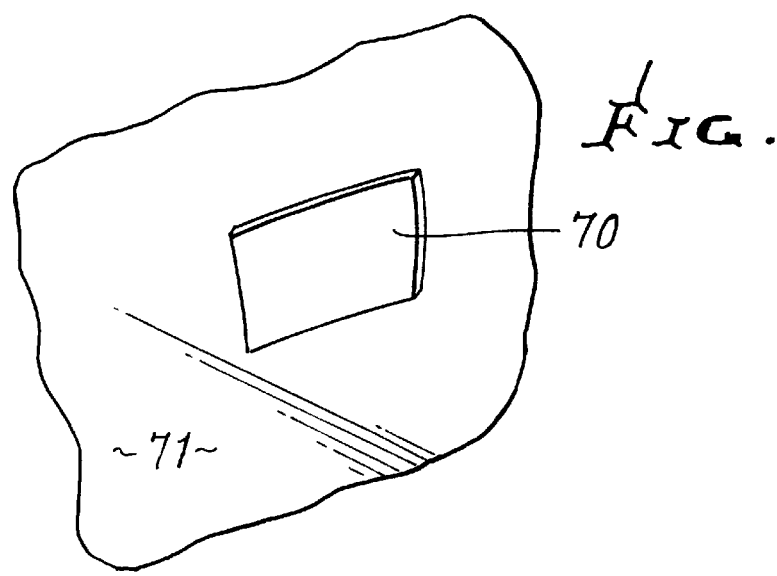
FIG. 6 is a plan view of a modified moisture receiver on a flexible carrier.
Figure 7:
FIG. 7 is a view like FIG. 6, but showing the carrier in the form of a flexible glove.

FIG. 6 shows a moisture receiver 70 on a flexible carrier sheet 71, adapted for receiving user's finger pressure to receive vaginal or other tissue moisture. FIG. 7 is similar to FIG. 6, but shows use of a flexible glove 73 with the receiver 70 carried by glove finger 74, for use with the indicators as in any of FIGS. 1–3.

Figure 8:
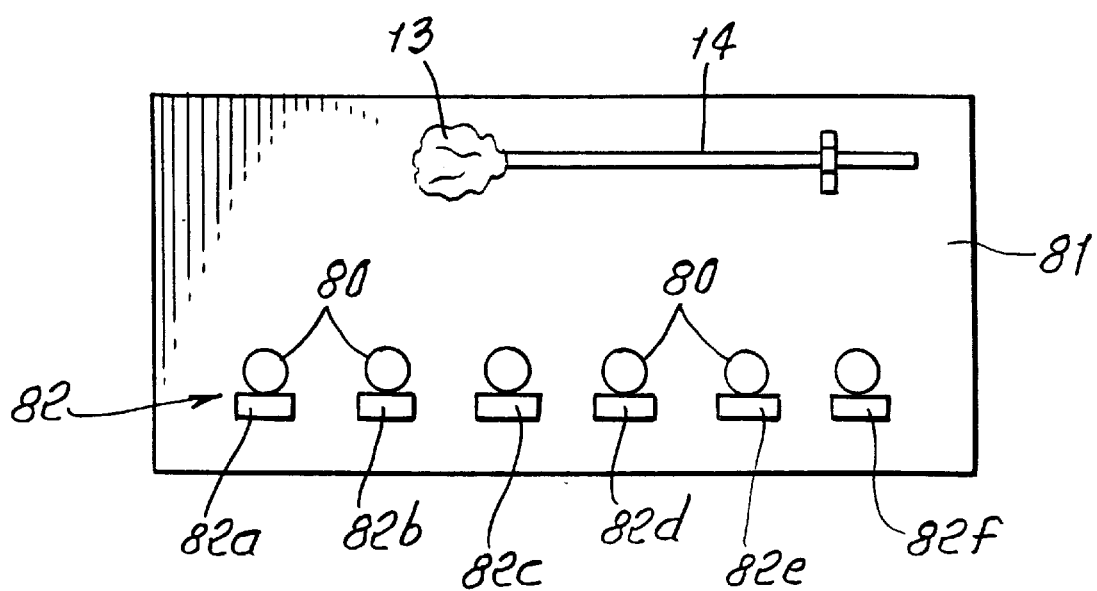
FIG. 8 is a plan view showing a still further modified kit, or package.

FIG. 8 is like FIG. 4, but shows a series of indicators 80 on a card 81, and with one color test band 82 adjacent each indicator. The bands 82 have different colors, and correspond to the color test bands 24a–24f seen in FIG. 2.

In the above, the term pH is a symbol relating the hydrogen ion ($H^+$) concentration or activity of a solution to that of a given standard solution. Numerically, the pH is approximately equal to the negative logarithm of $H^+$ concentration expressed in molarity. pH7 is neutral; above it alkalinity increases; and below it acidity increases.

The term "vaginal moisture" as used herein shall be understood as equivalent to urethral moisture. "pH" is a measure of acidity or alkalinity, of a solution or fluid, and equal to 7 for neutral solutions. pH increases with increasing alkalinity, and decreases with increasing acidity.

Referring again to FIGS. 1–3, the moisture sample to be tested as by moisture application to the indicators 11 and 21 may include or consist of amniotic fluid. That sample may be collected or employed in fluid form outside the body, as seen in FIG. 3a at 110 collected on a support 111, such fluid typically leaking at times from a pregnant woman onto a bed surface. Accordingly, transfer of the sample of collected moisture to the indicator 11 or 21 occurs outside the human body. As an example, the indicator may simply be dipped into contact with the sample of collected moisture. A support for the indicator may be provided, as by card 10 or card 20. That card can be manipulated to bring the indicator and fluid into wetting contact. More generally, the support maybe provided in one of the following forms: a stick, a card, or a receptacle. Also, a pH color comparison chart is typically provided, as in FIGS. 1 and 3 for example, and the indicator color can quickly be compared with colors on said chart.

The general method of testing for uterine membrane rupture accompanied by release of amniotic fluid, from the body, includes the steps:

a) providing a pH indicator, the indicator characterized as changing color as a function of fluid pH, b) contacting said pH indicator with fluid that has been released via the body vaginal zone or urethral zone, c) and observing the color of the indicator to determine occurrence of a color change indicative of the presence of amniotic fluid or of another body fluid such as urine.

The observing step 4 includes determining if the indicator color change is indicative of a pH at or close to 7.0, indicative of the presence of amniotic fluid. More specifically, observing includes determining:

i) if the indicator color change is indicative of a pH at or close to 7.0, indicative of the presence of amniotic fluid, or ii) if the indicator color change is indicative of a pH at or close to 4.5, indicating presence of urine.

I claim:

1. In the method of measuring pH of vaginal or other body tissue moisture, the steps that include a) providing an indicator that exhibits a characteristic color when contacted with vaginal or other tissue moisture, said color being a function of moisture pH, b) obtaining a vaginal or vaginal tissue moisture sample by providing a vaginal or vaginal tissue moisture receiver supported on a carrier, and manipulating the carrier to insert the receiver into the vagina and therein obtain said sample on the receiver, and thereafter withdrawing the receiver from the vagina and transferring that moisture from the sample to said indicator, outside the body, whereby the indicator then exhibits said characteristic color, which is a function of pH of said moisture, c) providing a color comparison measurement means, and comparing said indicator characteristic color with said color comparison measurement means.

2. The method of claim 1 including providing a vaginal or other moisture receiver supported on a carrier, and manipulating the carrier to obtain said sample on the receiver.

3. The method of claim 1 including providing a package which includes structure carrying said indicator and said color comparison measurement means.

4. The method of claim 2 including providing a package which includes structure supporting said indicator and said carrier for the receiver, and including the step of removing the carrier from the package for use in obtaining said moisture sample on the receiver.

5. The method of claim 3 wherein said color comparison measurement means is provided to extend proximate said indicator, in or on the package.

6. The method of claim 5 wherein said color comparison measurement means is provided to include portions of varying color that are arranged in at least one of the following ways:

ii) in a generally linear sequence, iii) in a sequence to at least partially surround the indicator.

7. The method of claim 5 wherein said color comparison measurement means is provided in the form of swatches of varying color that extend in a sequence about and proximate the indicator for side by side comparison with the color of the indicator.

8. The combination of claim 5 wherein the indicator includes multiple sections, and said color comparison measurement means is provided in the form of swatches of varying color that extend about and proximate each indicator section, for side-by-side comparison with the color of each indicator section.

9. The combination of claim 5 wherein the indicator includes multiple sections, and said color comparison measurement means includes color swatches, at least one swatch located proximate each indicator.

10. The method of claim 4 wherein the carrier is provided in the form of a stick, and the receiver is supported proximate an end of the stick, the receiver provided in the form of a swab, and a shoulder provided on the stick to limit depth of insertion of the swab, into the vagina.

11. The method of claim 4 wherein said indicator is provided in the form of a strip.

12. The method of claim 4 including providing a second indicator supported by the package, said second indictor including a reactant or reactants characterized as changing color when contacted with moisture containing amine, and including transferring moisture from the sample to said second indicator, outside the body, whereby a change in color at the second indicator indicates the presence of amine from pathogenic bacteria or flagelates or protozoa in said moisture.

13. The method of claim 12 wherein said second indicator is selected from the group consisting of Bromocresol Green, Bromocresol Purple, Nitrazine Yellow, Bromophenol Blue, and equivalents.

14. The method of claim 12 wherein said amine is selected from the group putrecine and cadavarine.

15. The method of claim 12 wherein said reactant includes an alkali substance selected from the group that consists essentially of potassium hydroxide, sodium aluminate, magnesium hydroxide, sodium hypochlorite and sodium carbonate.

16. The method of claim 1 including repeating said method at intervals and over a time period sufficient to detect changes in vaginal or other tissue moisture pH levels indicative of need for estrogen therapy.

17. The method of claim 1 wherein said moisture sample includes amniotic fluid.

18. The method of claim 17 wherein said moisture sample is collected in fluid form outside the body.

19. The method of claim 1 wherein said indicator is dipped into contact with the sample of collected moisture.

20. The method of claim 18 including providing a support for said indicator, and manipulating said support to bring said indicator and fluid into wetting contact.

21. The method of claim 20 wherein the support is provided in one of the following forms:
   a) a stick
   b) a card
   c) a receptacle.

22. The method of claim 17 including providing a pH color comparison chart, and comparing the indicator color with colors on said chart.

23. The method of claim 2, including adhering the receiver to the carrier, prior to said step b).

24. The method of claim 1 including locating said indicator in a predetermined position, proximate the color comparison measurement means.

25. The method of testing for uterine membrane rupture accompanied by release of amniotic fluid, from the body, that includes
   a) providing a pH indicator, the indicator characterized as changing color as a function of fluid pH,
   b) contacting said pH indicator with that fluid that has been obtained from within the vagina or urethra, or from vaginal tissue or urethral tissue within the vagina or urethra, and transported to the exterior of the vagina or urethra, for transfer to the indicator,
   c) and observing the color of the indicator to determine occurrence of a color change indicative of the pressure of amniotic fluid or of another body fluid such as urine.

26. The method of claim 25 including providing a support for said indicator, and manipulating said support to bring said indicator and fluid into wetting contact.

27. The method of claim 26 wherein the support is provided in one of the following forms:
   a) a stick
   b) a card
   c) a receptacle.

28. The method of claim 25 including providing a pH indicator color comparison chart, and comparing the indicator color with colors on said chart.

29. The method of claim 25 wherein said observing includes determining if the indicator color change is indicative of a pH at or close to 7.0, indicative of the presence of amniotic fluid.

30. The method of claim 25 wherein said observing includes determining:
   i) if the indicator color change is indicative of a pH at or close to 7.0, indicative of the presence of amniotic fluid, or
   ii) if the indicator color change is indicative of a pH at or close to 4.5, indicating presence of urine.

31. The method of claim 26 including adhering the indicator to the support prior to said step b).

* * * * *